United States Patent [19]
Clark et al.

[11] Patent Number: 5,330,998
[45] Date of Patent: Jul. 19, 1994

[54] THIAZOLIDINEDIONE DERIVATIVES AS HYPOGLYCEMIC AGENTS

[75] Inventors: David A. Clark, East Lyme; Steven W. Goldstein, Mystic; Bernard Hulin, Essex, all of Conn.

[73] Assignee: Pfizer Inc., New York, N.Y.

[21] Appl. No.: 566,437

[22] PCT Filed: Mar. 8, 1988

[86] PCT No.: PCT/US88/00745

§ 371 Date: Aug. 14, 1990

§ 102(e) Date: Aug. 14, 1990

[51] Int. Cl.[5] .................. A61K 31/425; C07D 417/12
[52] U.S. Cl. ................................ 514/369; 514/342; 546/280; 548/183
[58] Field of Search .................. 548/183; 546/280; 514/369, 342

[56] References Cited

U.S. PATENT DOCUMENTS

| | | | |
|---|---|---|---|
| 4,287,200 | 9/1981 | Kawamatsu et al. | 424/270 |
| 4,617,312 | 10/1986 | Schnur | 514/369 |
| 4,703,052 | 10/1987 | Eggler et al. | 514/337 |
| 4,725,610 | 2/1988 | Meguro et al. | 514/369 |
| 4,775,687 | 10/1988 | Meguro et al. | 514/369 |

OTHER PUBLICATIONS

Sohda et al. Chem. Pharm. Bull. Japan, vol. 30 pp. 3580-3600 (1982).
Burger, Alfred, *Medicinal Chemistry*, vol. 3, 3rd Ed., pp. 64-80, Wiley-Interscience (1970).

*Primary Examiner*—Robert Gerstl
*Attorney, Agent, or Firm*—Peter C. Richardson; Gregg C. Benson; Mervin E. Brokke

[57] ABSTRACT

Hypoglycemic thiazolidine-2,4-dione derivatives of the formula

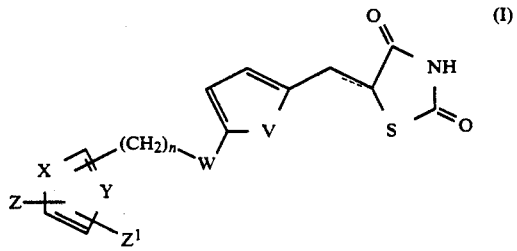

wherein
the dotted line represents a bond or no bond;
V is —CH=CH—, —N=CH—, —CH=N—, S, O or NR;
W is S, SO, $SO_2$, $SO_2NR^1$, $NR^1SO_2$, $CONR^1$ or $NR^1CO$;
X is S, O, $NR^2$, —CH=N— or —N=CH;
Y is CH or N;
Z is hydrogen, ($C_1$-$C_7$)alkyl, ($C_3$-$C_7$)cycloalkyl, phenyl, pyridyl, furyl, thienyl or phenyl mono- or disubstituted with the same or different groups which are ($C_1$-$C_3$)alkyl, trifluoromethyl, ($C_1$-$C_3$)alkoxy, fluoro, chloro or bromo;
$Z^1$ is hydrogen or ($C_1$-$C_3$)alkyl;
R, $R^1$ and $R^2$ are each independently hydrogen or ($C_1$-$C_4$); and
n is 1, 2 or 3;

a pharmaceutically acceptable cationic salt thereof; or a pharmaceutically acceptable acid addition salt thereof when the compound contains a basic nitrogen.

28 Claims, No Drawings

THIAZOLIDINEDIONE DERIVATIVES AS HYPOGLYCEMIC AGENTS

BACKGROUND OF THE INVENTION

The present invention relates to certain compounds of the formula (I), depicted below, having utility as hypoglycemic and hypocholesterolemic agents, methods for their use and pharmaceutical compositions containing them.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in the urine or in the blood. The administration of an excess dose of insulin causes hypoglycemia, with effects ranging from mild abnormalities in blood glucose or coma, or even death. Treatment of non-insulin dependent diabetes mellitus (Type II diabetes) usually consists of a combination of diet, exercise, oral agents, e.g., sulfonylureas, and in more severe cases, insulin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

Furthermore, atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295,369-377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion which accounts for the the arterial occlusion and tendency toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057–1080].

Schnur, U.S. Pat. No. 4,367,234 discloses hypoglycemic oxazolidinediones of the formula

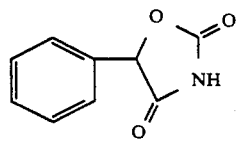

in which the phenyl ring is generally mono- or multisubstituted in the ortho/meta positions. Notably, with the exception of the 4-fluorophenyl analog, the parasubstituted derivatives are either inactive or possess a low level of hypoglycemic activity. Schnur, U.S. Pat. Nos. 4,332,952 and 4,342,771 further disclose a variety of similar oxazolidinedione hypoglycemic agents which are alternatively substituted at the 5-position with a heterocyclic group. These include certain furan, thiophene, pyrrole and pyridine derivatives.

Schnur, U.S. Pat. No. 4,617,312 discloses hypoglycemic thiazolidinediones of the formula

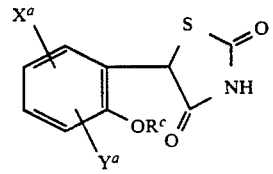

where $R^c$ is lower alkyl, $X^a$ is F, Cl or Br, and $Y^a$ is hydrogen, chloro, lower alkyl or lower alkoxy. Notably, the compounds require ortho-substitution with an alkoxy group, and para-substitution is limited to hydrogen or halogen.

Kawamatsu et al., U.S. Pat. No. 4,340,605, disclose hypoglycemic compounds of the formula

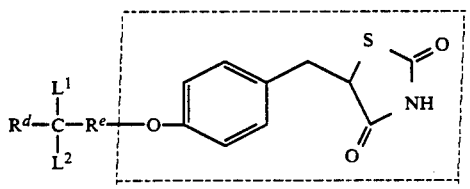

wherein $R^e$ is a bond or lower alkylene and when $R^d$ is an optionally substituted five- or six-membered heterocyclic group including one or two hetero-atoms selected from N, O and S, $L^1$ and $L^2$ may each be defined as hydrogen. Based on the lack of hypoglycemic and plasma triglyceride lowering activity of certain non-ether analogs, it has been suggested that the boxed portion of the structural formula, *including the ether oxygen*, represents an essential feature for useful activity in this series of compounds; Sohda et al., Chem. Pharm. Bull. Japan, Vol. 30, pp. 3580-3600 (1982).

Sohda et al. also describe the compound of the formula

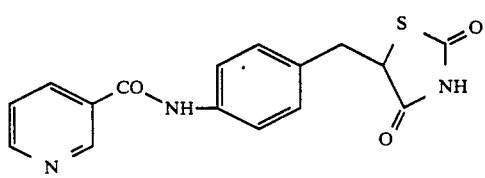

as having weak hypoglycemic and plasma triglyceride lowering activity.

Eggler et al., U.S. Pat. No. 4,703,052, discloses hypoglycemic thiazolidinediones of the formula

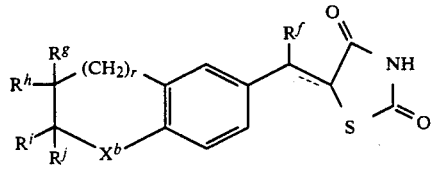

where the dotted line represents an optional bond, $R^f$ is H, methyl or ethyl, $X^b$ is O, S, SO$_2$, CH$_2$, CO, CHOH or NR$^k$, R$^k$ is H or an acyl group and the numerous definitions of $R^g$, $R^h$, $R^i$ $R^j$ include $R^g$, $R^h$ and $R^i$ as hydrogen or methyl and $R^j$ as optionally substituted phenyl, benzyl, phenethyl or styryl.

SUMMARY OF THE INVENTION

The present invention is directed to compounds having the formula

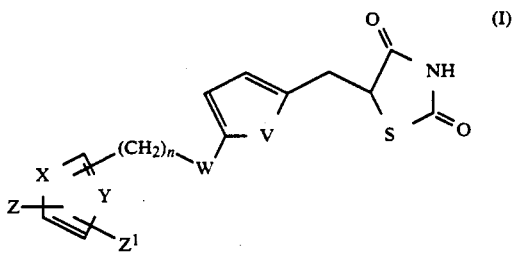

wherein the dotted line represents a bond or no bond;
V is —CH=CH—, —N=CH—, —CH=N—, S, O or NR;
W is S, SO, SO$_2$, SO$_2$NR$^1$, NR$^1$SO$_2$, CONR$^1$ or NR$^1$CO;
X is S, O, NR$^2$, —CH=N— or —N=CH;
Y is CH or N;
Z is hydrogen, (C$_1$-C$_7$)alkyl, (C$_3$-C$_7$)cycloalkyl, phenyl, pyridyl, furyl, thienyl or phenyl mono- or disubstituted with the same or different groups which are (C$_1$-C$_3$)alkyl, trifluoromethyl, (C$_1$-C$_3$)alkoxy, fluoro, chloro or bromo;
Z$^1$ is hydrogen or (C$_1$-C$_3$)alkyl;
R, R$^1$ and R$^2$ are each independently hydrogen or (C$_1$-C$_4$) alkyl; and
n is 1, 2 or 3;
the pharmaceutically acceptable cationic salts thereof; and the pharmaceutically acceptable acid addition salts thereof when the compound contains a basic nitrogen.

Based upon their level of activity and ease of preparation, preferred compounds are those wherein the dotted line represents no bond, particularly those wherein V is —CH=CH—, n is 1 or 2, W is NR$^1$CO, CONR$^1$, S or SO$_2$; and X is O and Y is N forming a 4-oxazolyl group; most particularly when Z is 2-phenyl and Z$^1$ is 5-methyl.

The expression "pharmaceutically-acceptable cationic salts" is intended to define but not limited to such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanoiamine, ethylenediamine, meglumine (N-methylglucamine), benethamine (N-benzylphenethylamine) diethylamine, piperazine, tromethamine (2-amino-2-hydroxymethyl-1,3-propanediol) and procaine. An especially preferred such salt is the sodium salt.

The expression "pharmaceutically-acceptable acid addition salts" is intended to define but not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Also embraced by the present invention are pharmaceutical compositions for use in treating a hyperglycemic mammal or a hypercholesterolemic mammal which comprises a blood glucose lowering amount or a blood cholesterol lowering amount of a compound of formula (I) and a pharmaceutically-acceptable carrier. The invention further comprises a method of lowering blood glucose in a hyperglycemic mammal which comprises administering to said mammal a blood glucose lowering effective amount of a compound of formula (I); and a method of lowering blood cholesterol in a hypercholesterolemic mammal which comprises administering to said mammal a blood cholesterol lowering amount of a compound of the formula (I).

DETAILED DESCRIPTION OF THE PRESENT INVENTION

The compounds of the formula (I) of the present invention are readily prepared. Most generally, the compounds of the formula (I) wherein the dotted line represents a bond are prepared by reaction of thiazolidine-2,4-dione with an aldehyde of the formula

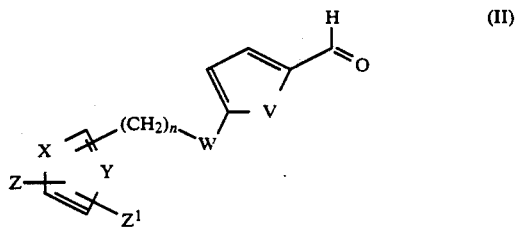

wherein V, W, X, Y, Z, $Z^1$ and n are as defined above. In this step, the reactants are heated in the presence of an excess of a mild base to provide the olefin of formula (I) wherein the dotted line represents a bond. Usually a 10-50% molar excess of one of the two reactants is employed, in order to force the reaction to completion within a reasonable period of time. In the present instance, it is generally preferred to use the readily available thiazolidine-2,4-dione in excess. In a preferred method the aldehyde of the formula (II) and the thiazolidinedione are coupled in the presence of a catalytic amount of a secondary amine, preferably pyrrolidine or piperidine, usually about 0.05 to 0.20 molar equivalents, in a reaction-inert solvent such as a lower alkanol (e.g., methanol, ethanol, n-propanol, isopropanol). Temperature is not especially critical, but will generally be above room temperature to effect reasonably rapid completion of the reaction, but below 100° C. to minimize possible side reactions. Reflux temperature of the lower alkanol solvent is particularly convenient.

As used here and elsewhere herein, the expression "reaction inert solvent" refers to a solvent which does not interact with starting materials, reagents, intermediates or products in a manner which adversely affects the yield of the desired product.

In an alternative method the aldehyde of the formula (II) and thiazolidine-2,4-dione are intimately mixed with a molar excess, preferably a 2-4 fold molar excess, of anhydrous sodium acetate and the mixture is heated at a temperature high enough to effect melting, generally about 140°-170° C., at which temperature the reaction is substantially complete in from about 5 to 60 minutes. The desired olefin of formula (I) wherein the dotted line represents a bond is then isolated, for example, by mixing with water and filtration, to obtain the crude product, which is purified, if desired, e.g., by crystallization or by standard chromatographic methods.

The resulting olefinic products are active hypoglycemic agents, but also serve as intermediates for preparation of the corresponding reduced compounds of formula (I) wherein the dotted line represents no bond. While the reduction of the above olefins may be carried out by employing a number of reducing agents which are known to reduce carbon-to-carbon double bonds, the preferred methods employ hydrogen in the presence of a noble metal catalyst, sodium amalgam in methanol, or zinc in acetic acid.

When the reduction step is carried out employing hydrogen in the presence of a noble metal catalyst, a convenient method for carrying out this transformation is to stir or shake a solution of the olefinic compound of the formula (I) wherein the dotted line represents a bond in a reaction-inert solvent under an atmosphere of hydrogen, or hydrogen mixed with an inert diluent such as nitrogen, in the presence of a noble metal hydrogenation catalyst. Suitable solvents for this reaction are those which substantially dissolve the starting compound but which do not themselves suffer hydrogenation or hydrogenolysis. Examples of such solvents include ethers such as diethyl ether, tetrahydrofuran, dioxane and 1,2-dimethoxyethane; low molecular weight amides such an N,N-dimethylformamide, N-N-dimethylacetamide and N-methylpyrrolidone; and lower alkyl carboxylic acids such as formic, acetic, propionic and isobutyric acid. Especially preferred such solvents are tetrahydrofuran and acetic acid. Hydrogenation is particularly preferred when W is other than S or SO.

Introduction of the hydrogen gas into the reaction medium is usually accomplished by carrying out the reaction in a sealed vessel, containing the olefinic compound, solvent, catalyst and hydrogen. The pressure inside the reaction vessel can vary from about 1 to about 100 kg/cm². The preferred pressure range, when the atmosphere inside the reaction vessel is substantially pure hydrogen, is from about 2 to about 5 kg/cm². The hydrogenation is generally run at a temperature of from about 0° to about 60° C., and preferably from about 25° to about 50° C. Utilizing the preferred temperature and pressure values, hydrogenation generally takes place in a few hours, e.g., from about 2 hours to about 20 hours. The preferred noble metal catalysts used in this hydrogenation reaction are the type of agents known in the art for this kind of transformation, for example, palladium, platinum and rhodium. A palladium catalyst is preferred because such catalysts are not readily poisoned by sulfur. The catalyst is usually present in an amount from about 0.01 to about 25 weight-percent, and preferably from about 0.1 to about 10 weight-percent, based on the olefinic compound. It is often convenient to suspend the catalyst on an inert support; a particularly convenient catalyst is palladium suspended on an inert support such as carbon.

When the hydrogenation of the methylene double bond is substantially complete, the desired product of formula (I) wherein the dotted line is no bond is then isolated by standard methods, e.g., the catalyst is recovered by filtration, the solvent evaporated and the product purified, if desired, by well known methods such as crystallization or by chromatography.

An alternative method for reduction of the olefinic compounds of the formula (I) wherein the dotted line represents a bond is conventional sodium amalgam reduction in methanol, usually at or about ambient temperature; or zinc dust in acetic acid, usually at elevated temperature, conveniently at the reflux temperature of the reaction mixture. Both of these methods, which are preferred when W is S, are exemplified below.

Those compounds wherein W is SO or $SO_2$ are alternatively (and preferably when W is SO) formed by suitable oxidation of the corresponding compounds where W is S. When the sulfoxide is desired, the sulfide is preferably oxidized with at least one molar equivalent (usually a 2-3 fold molar excess) of sodium periodate in a reaction inert solvent such as aqueous methanol, generally at room temperature or below so as to avoid over oxidation. Alternatively, close to one molar equivalent of m-chloroperbenzoic acid can be used for this purpose, in a reaction-inert solvent such as methylene chloride or toluene, generally at reduced temperature such as $-10°$ to $10°$ C. When the sulfone is desired, a convenient oxidant is at least two molar equivalents of said m-chloroperbenzoic acid, otherwise in the same solvents and under the same mild conditions specified in the preceding sentence. However, a less expensive oxidant for formation of the sulfone is $H_2O_2$, generally used in excess in a reaction inert solvent such as acetic acid.

When a saturated compound of the formula (I) wherein the dotted line represents no bond is desired, an alternative synthetic route is to react thiazolidine-2,4-dione with a compound of the formula

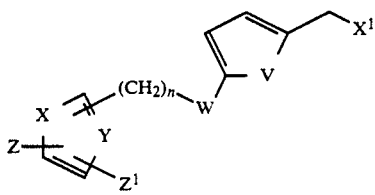

wherein V, W, X, Y, Z, $Z^1$ and n are as defined above, and $X^1$ is a nucleophilic leaving group such as chloride, bromide, iodide or mesylate. These reactants are generally used in substantially equimolar quantities, although 10-25% excess of readily available thiazolidine-2,4-dione is preferred in order to force the reaction to completion within a reasonable period of time. The reaction is carried out in the presence of reaction-inert solvent, such as tetrahydrofuran, with the thiazolidine-2,4-dione prereacted with two molar equivalents of a strong base such as butyl lithium in order to preform the dianion. Salt formation is generally carried out at reduced temperature (e.g. $-50°$ to $-80°$ C.); the reactants mixed at an intermediate temperature, and reaction carried to completion at an elevated temperature (e.g. the reflux temperature of the reaction mixture). It will be evident to those skilled in the art that this method will be preferred only when there are no other reactive groups (e.g., NH) present in the compound of the formula (III). Thus, when V is NH, this group will generally be in protected form, e.g., as an N-benzyl group which is subsequently removed by conventional hydrogenolysis conditions such as those described above.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

Thiazolidine-2,4-dione is commercially available. The aldehydes of formula (II) are prepared by a variety of conventional methods; for example, by mild oxidation of the corresponding primary alcohol with reagents such as manganese dioxide under conditions known to produce aldehydes from primary alcohols; reaction of the corresponding aralkyl bromides with n-butyl lithium followed by N,N-dimethylformamide at $-80°$ to $-70°$ C., reaction of a suitably 4-substituted benzaldehyde (or corresponding thiophene or pyridine analog) with a suitably substituted heterocyclic derivate so as to form the bridging group:

$$-(CH_2)_n-W-$$

For example, with the aldehyde group optionally in protected form or in the form of an aldehyde precursor.

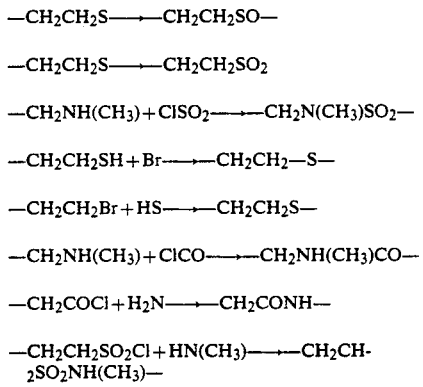

The halides/mesylates of the formula (III) are also available by conventional methods, such as by the action of a suitable reagent (e.g., $PBr_3$, $CH_3SO_2Cl$ on the corresponding alcohol), halogenation of a corresponding methyl derivative, and so forth.

It will be further evident to those skilled in the art that the synthesis of a compound of the formula (I) can be varied by the coupling of a precursor aldehyde (or mesylate/halide) with thiazolidine-2,4-dione, with completion of the side chain as a later step by one of the synthetic methods for aldehydes of the formula (II) which are illustrated above.

The present compounds of the formula (I) are readily adapted to clinical use as hypoglycemic or hypocholesterolemic agents. The activity required for the former clinical use is defined by the test for hypoglycemic effect in ob/ob mice by the following procedure:

Five to eight week old C57 BL/6J-ob/ob mice (obtained from Jackson Laboratory, Bar Harbor, Me.) were housed five per cage under standard animal care practices. After a one week acclimation period, the animals were weighed and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5-50 mg/kg), a positive control (50 mg/kg) of ciglitazone; U.S. Pat. No. 4,467,902; Sohda et al., Chem. Pharm. Bull., vol. 32, pp. 4460-4465, 1984), or vehicle. All drugs were administered in a vehicle consisting of 0.25% w/v methyl cellulose. On day 5, the animals were weighed again and bled (via the ocular route) for blood metabolite levels. The freshly collected samples were centrifuged for two minutes at 10,000 xg at room temperature. The supernatant was analyzed for glucose, for example, by the ABA 200 Bichromatic Analyzer ™, using the A-gent ™ glucose UV reagent system* (hexokinase method) using 20, 60 and 100 mg/dl standards. Plasma glucose was then calculated by the equation, Plasma glucose (mg/dl) = Sample value $\times 5 \times 1.67 = 8.35 \times$ Sample value where 5 is the dilution factor and 1.67 is the plasma hematocrit adjustment (assuming the hematocrit is 40%). ™ A registered trademark of Abbott Laboratories, Diagnostics Division, 820 Mission Street, So. Pasadena, Calif. 91030.
*A modification of the method of Richterich and Dauwalder, Schweizerische Medizinische Wochenschrift, 101,860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Studies such as that described below demonstrate that the compounds of formula (I) effect the lowering of serum cholesterol levels in mammals.

Female mice (strain C57Br/cd J), obtained from Jackson Laboratories, Bar Harbor, Maine, are used at age 8-12 weeks, following 2-4 weeks acclimation having free access to water and standard laboratory chow. Animals are divided randomly into three groups of 6-7 animals. All three groups are placed on a diet containing 0.75% cholesterol, 31% sucrose, 15.5% starch, 20% casein, 17% cellulose, 4.5% corn oil, 5% coconut oil, 0.25% cholic acid, 4% salts and 2% vitamin; permitted to feed ad lib for 18 days; and dosed daily at 9-11 a.m. for the final 5 days by oral gavage, the control group with 5 ml/kg of vehicle (0.1% aqueous methyl cellulose) and the test groups with the compound under study at a dose range of 0.1-20 mg/kg/day in vehicle. After the fourth day of dosing, the animals are fasted overnight, starting at 5 p.m. The following morning a fifth and final dose of the compound is administered to the test groups and, three hours later, the animals are sacrificed by decapitation. Blood from the body trunk is collected and allowed to clot, and the serum assayed enzymatically, using an Abbott VP automated analyzer, for HDL cholesterol, LDL and VLDL cholesterol, and total cholesterol. Whether judged on the basis LDL+VLDL cholesterol levels, total cholesterol levels or the ratio of LDL+VLDL/HDL, the compounds of this invention generally show favorable result in lowering cholesterol levels.

The present compounds of the formula (I) are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or pharmaceutically acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. The injectable solutions prepared in this manner can then be administered intravenously, intraperitoneally, subcutaneously, or intramuscularly, with intramuscular administration being the preferred parenteral route in man.

The present invention is illustrated by the following Examples. However, it should be understood that the invention is not limited to the specific details of these examples. Nomenclature used herein is based on Rigaudy and Klesney, IUPAC Nomenclature of Organic Chemistry, 1979 Ed., Pergammon Press, New York, 1979. The abbreviations THF, DMF and DMSO refer to tetrahydrofuran, dimethylformamide and dimethylsulfoxide respectively.

EXAMPLE 1

N-[(5-Methyl-2-phenyl-4-oxazolyl)methyl]-4-[(thiazolidine-2,4-dion-5-yl)methyl]benzenesulfonamide 4-[(Thiazolidine-2,4-dion-5-yl)methyl]benzenesulfonyl chloride (1.62 g, 5.31 mmol) in 25 mL of $CH_2Cl_2$ was cooled to 0° C. N-[(5-Methyl-2-phenyl-4-oxazolyl)-methyl]amine (1.0 g, 5.31 mmol) in 10 mL of $CH_2Cl_2$ was added dropwise, followed by diisopropylethylamine (1.1 mL, 6.37 mmol) and the mixture stirred at 0° C. for 20 minutes, then at room temperature for 18 hours. The reaction mixture was diluted with 20 mL $CH_2Cl_2$, washed 3×25 mL 1N HCl, 1×25 mL 5% $NaHCO_3$ and 2×25 mL brine, dried ($MgSO_4$) and stripped to 1.9 g of solids. The latter was flash chromatographed on silica gel using 3:40 ethyl acetate:hexane as eluant to yield 0.34 g of purified, present title product, mp 120°–122° C.

EXAMPLE 2

N-Methyl-N-[(5-Methyl-2-phenyl-4-oxazolyl)-methyl]-4-[(thiazolidine-2,4-dion-5-yl)-methyl]benzenesulfonamide Using 1:19 $CH_3OH:CHCl_3$ as eluant, otherwise by the method of the preceding Example, N-methyl-N-[(5-methyl-2-phenyl-4-oxazolyl) methyl]amine (0.39 g, 1.93 mmol) was converted to present chromatographed title product rag; tlc Rf 0.35 (1:19 $CH_3OH:CHCl_3$). The latter (150 rag, 0.954 mmol) was dissolved in 10 mL of methanol and $NaOCH_3$ (51.6 rag, 0.954 mmol) added. After stirring for 15 minutes, the solution was stripped to yield the sodium salt of present title product; mp 250° C. (dec).

EXAMPLE 3

N-[(5-Methyl-2-phenyl-4-oxazolyl)methyl]-4-[(thiazolidine-2,4-dion-5-ylidene)methyl]benzamide 4-[(5-Methyl-2-phenyl-4-oxazolyl)methylaminocaronyl]benzaldehyde (0.880 g, 2.75 mmol), thiazolidine-2,4-dione (0.483 g, 4.12 mmol) and sodium acetate (0.676 g, 8.24 mmol) were intimately mixed and heated at 140°–145° C. for 45 minutes, then cooled to room temperature, the solids triturated and stirred with mL of water for 30 minutes and 1.20 g of present title product recovered by filtration; mp 235°–237° C. (dec); tlc Rf 0.2 (3:1 ethyl acetate:hexane).

EXAMPLE 4

N-Methyl-N-[(5-methyl-2-phenyl-4-oxazolyl)methyl]-4-[(thiazolidine-2,4-dion-5-ylidene)methyl]benzamide By the method of the preceding Example, except to use a heating time of 2 hours, 4-[N-[(5-methyl-2-phenyl-4-oxazolyl)methyl]methylaminocarbony-1]benzaldehyde (0.520 g, 1.56 mmol) was converted to 0.61 g of present title product; mp 95°–98° C.; tlc Rf 0.2 (3:1 ethyl acetate:hexane).

EXAMPLE 5

N-[(5-Methyl-2-phenyl-4-oxazolyl)methyl]-4-[[(thiazolidine-2,4-dion-5-yl)methyl]benzamide Title product of Example 3 (0.60 g, 1.43 mmol) in a mixture of 70 mL of THF and 50 mL of acetic acid was hydrogenated over 1.0 g of 10% Pd/C sulfur resistant catalyst in a Paar shaker at 50 psig and room temperature for 1 hour. Catalyst was recovered by filtration over diatomaceous earth with THF wash. The filtrate and wash liquor were combined, stripped to a gummy solid, taken up in $CHCl_3$ and sufficient $CCl_4$ added to precipitate 0.35 g of present title product; mp 49°–53° C.; tlc Rf 0.7 (3:1 ethyl acetate:hexane).

EXAMPLE 6

N-Methyl-N-[(5-methyl-2-phenyl-4-oxazolyl)methyl]-4-[(thiazolidine-2,4-dion-5-yl)methyl]benzamide Title product of Example 4 (0.30 g, 0.69 mmol) in 80 mL THF and 25 mL acetic acid was hydrogenated over 0.80 g of 10% Pd/C sulfur resistant catalyst in a Paar shaker at 50 psig and room temperature for 2 hours. Catalyst and crude product were recovered as in the preceding Example. The crude product was flash chromatographed on silica gel using 3:1 ethyl acetate:hexane as eluant to yield 81 mg of present title product; mp 75°–78° C.; tlc Rf 0.45 (3:1 ethyl acetate:hexane).

EXAMPLE 7

5-[4-[2-(5-Methyl-2-phenyl-4-oxazolyl)acetamido]benzyl]thiazolidine-2,4-dione 2-(5-Methyl-2-phenyl-4-oxazolyl) acetic acid (0.40 g, 1.8 mmol) dissolved in 5 mL of $CH_2Cl_2$ was cooled to 0°–5° C. Triethylamine (0.46 mL) and then ethyl chloroformate (0.30 mL) were each added dropwise. After stirring at 15 minutes at 0° C. to assure complete conversion of the acid to the intermediate mixed anhydride, a solution of 5-(4-aminobenzyl) thiazolidine-2,4-dione (0.71 g, 3.2 mmol; Chem. Pharm. Bull. Japan, v. 30, p. 3580, 1982) and 0.24 mL triethylamine in 15 mL were added dropwise as the temperature was maintained at 0°–5° C. The resulting solution was then stirred for 18 hours at room temperature, stripped of solvent and the residue distributed between 25 mL 2N HCl and 25 mL ethyl acetate. The aqueous layer was extracted with 25 mL additional ethyl acetate, and the organic layers combined, washed sequentially 1×30 mL water, 1×30 mL saturated $NaHCO_3$ and 1×30 mL saturated NaCl, dried ($Na_2SO_4$) and stripped to yield 0.84 g of solids. The latter was flash chromatographed on silica gel using 1:2 ethyl acetate:hexane as eluant to yield 0.23 g of impure title product suitable for rechromatography and 0.20 g of purified title product.

EXAMPLE 8

5-[4-[2-(5-Methyl-2-phenyl-4-oxazolyl) ethylthio]phenylmethylene]thiazolidine-2,4-dione Using a temperature of 170° C. and a heating time of 0.5 hour, the method of Example 3 was used to convert 4-[2-(5-methyl-2-phenyl-4-oxazolyl) ethylthio]benzaldehyde (0.235 g, 0.73 mmol) to 0.15 g of present title product; tlc Rf 0.26 (1:39 $CH_3OH:CH_2Cl_2$).

EXAMPLE 9

5-[4-[2-(5-Methyl-2-phenyl-4-oxazolyl) ethylthio]benzyl]thiazolidine-2,4-dione

1% Na/Hg (2.60 g) and the title product of the preceding Example (0.15 g) were combined in 15 mL of $CH_3OH$, stirred 4 hours at room temperature and decanted. The decant was stripped, the residue taken up in 25 mL of water, acidified to pH 2 with 2N HCl and extracted 3×20 mL $CH_2Cl_2$. The organic layers were combined, dried ($K_2CO_3$) and stripped to an 81 mg residue which was plug filtered on silica gel using 1:39 $CH_3OH:CH_2Cl_2$ as eluant to yield 58 mg of present title product; tlc Rf 0.46 (1:39 $CH_3OH:CH_2Cl_2$), 0.6 (1:20 $CH_3OH:CH_2Cl_2$).

EXAMPLE 10

5-[4-[2-(5-Methyl-2-phenyl-4-oxazolyl)ethylsulfonyl]-benzyl]oxazolidine-2,4-dione Title product of the preceding Example (53 mg, 0.125 mmol) was dissolved in 5 mL of $CH_2Cl_2$ and cooled to 0° C. m-Chloroperbenzoic acid (58 mg, 0.275 mmol) was added portionwise over 0.5 hour at 0° C. The mixture was then stirred 2 hours at room temperature, diluted with 10 mL $CH_2Cl_2$, washed with 10 mL 5% NaHCO 25 and 10 mL brine, dried ($MgSO_4$) and stripped to yield 27 mg of title product as a white foam; tlc Rf 0.50 (1:19 $CH_3OH:CH_2Cl_2$).

EXAMPLE 11

5-[4-[2-(5-Methyl-2-phenyl-4-oxazolyl)ethylsulfinyl)benzyl]thiazolidine-2,4-dione Title product of Example 9 (5.8 mmol) is dissolved in methanol (125 mL) and added to sodium periodate (17.4 mmol, 3.7 g) dissolved in water (40 mL) at room temperature. The reaction mixture is stirred for 1 hour and then concentrated to 50 mL. Water (150 mL) is added and the solution is extracted with ethyl acetate ($2 \times 125$ mL). The organic layers are washed with water (50 mL), saturated NaCl (50 mL), dried ($NaSO_4$) and solvent removed in vacuo to yield present title product.

EXAMPLE 12

Sodium Salt of 5-[4-[2-(5-Methyl-2-phenyl-4-oxazolyl)ethylthio]benzyl]thiazolidine-2,4-dione Title product of Example 9 (6.9 mmol) is dissolved, with warming as necessary, in 75 mL of ethyl acetate. Sodium 2-ethylhexanoate (6.9 mmol, 1.1 g) in 10 mL ethyl acetate is added. After standing overnight, present title product is recovered by filtration.

EXAMPLE 13

5-[4-[(5-Methyl-2-phenyl-4-oxazolyl)methylsulfonylamino]benzyl]thiazolidine-2,4-dione By the method of Example 7, 2-(5-methyl-2-phenyl-4-oxazolyl)methanesulfonic acid is converted to present title product.

EXAMPLES 14–20

5-[4-(2-(5-Methyl-2-(substituted)-4-oxazolylacetamido]benzyl]-thiazolidine-2,4-dione By substituting the appropriate 2-[5-methyl-2-(substituted)-4-oxazolyl]acetic acid in the method of Example 7, the following additional title products are produced.

| Example No. | 2-Substituent |
| --- | --- |
| 14 | 4-methoxyphenyl |
| 15 | 2,5-dichlorophenyl |
| 16 | 3-fluoro-4-methylphenyl |
| 17 | 2-thienyl |
| 18 | 2-furyl |
| 19 | 3-furyl |
| 20 | 5-bromo-2-furyl |

EXAMPLE 21

5-[4-[3-(5-Methyl-2-(substituted)-4-oxazolyl)propionamido]benzylthiazolidine-2,4-dione Present title product is prepared by substituting 3-(5-methyl-2-phenyl-4-oxazolyl)propionic acid in the method of Example 7.

EXAMPLE 22

5-[4-[(5-Methyl-2-phenyl-4-oxazolyl)methylthio]-phenylmethylene]thiazolidine-2,4-dione 4-[(5-Methyl-2-phenyl-4-oxazolyl)methylthio]benzaldehyde (0.05 mol), thiazolidine-2,4-dione (11.7 g, 0.10 mol and piperidine (0.85 g, 0.01 mol) are combined in 300 mL absolute ethanol, and the mixture refluxed for 24 hours, cooled to 0° C., diluted slowly with 600 mL of ether and, after stirring for 1 hour at 0° C. present title recovered by filtration. If desired, the product is triturated with 150 mL of warm acetic acid (40°–50° C.). The resulting slurry is cooled to room temperature, diluted with 300 mL of ether, and purified title product recovered by filtration.

EXAMPLES 23–34

5-[4-[(Heteroaryl)methylthio]phenylmethylene]-thiazolidine-2,4-diones

By substituting the appropriate 4-[(heteroaryl)methylthio]benzaldehyde in the method of the Example, the following title compounds are prepared:

| Example No. | Heteroaryl Group |
| --- | --- |
| 23 | 2-phenyl-4-oxazolyl |
| 24 | 2-(4-methoxyphenyl)-5-methyl-4-oxazolyl |
| 25 | 2-(2-thienyl)-5-methyl-4-oxazolyl |
| 26 | 2-(2-furyl)-5-methyl-4-oxazolyl |
| 27 | 2-cyclohexyl-5-methyl-4-oxazolyl |
| 28 | 2-phenyl-4-thiazolyl |
| 29 | 4-methyl-2-phenyl-5-thiazolyl |
| 30 | 2-pyridyl |
| 31 | 4-pyridyl |
| 32 | 5-phenyl-2-furyl |
| 33 | 5-phenyl-2-thienyl |
| 34 | 1-methyl-5-phenyl-2-pyrrolyl |

EXAMPLES 35–47

5-[4-[(Heteroaryl)methylthio]benzylthiazolidine-2,4-diones

By the method of Example 9, the products of Examples 22–34 are converted to the present title products:

| Example No. | Heteroaryl Group |
| --- | --- |
| 35 | 5-methyl-2-phenyl-4-oxazolyl |
| 36 | 2-phenyl-4-oxazolyl |
| 37 | 2-(4-methoxyphenyl)-5-methyl-4-oxazolyl |
| 38 | 2-(2-thienyl)-5-methyl-4-oxazolyl |
| 39 | 2-(2-furyl)-5-methyl-4-oxazolyl |
| 40 | 2-cyclohexyl-5-methyl-4-oxazolyl |
| 41 | 2-phenyl-4-thiazolyl |
| 42 | 4-methyl-2-phenyl-5-thiazolyl |
| 43 | 2-pyridyl |

-continued

| Example No. | Heteroaryl Group |
|---|---|
| 44 | 4-pyridyl |
| 45 | 5-phenyl-2-furyl |
| 46 | 5-phenyl-2-thienyl |
| 47 | 1-methyl-5-phenyl-2-pyrrolyl |

EXAMPLE 48

5-[4-[3-(5-Methyl-2-phenyl-4-oxazolyl)propylthio]-phenylmethylene]thiazolidine-2,4-dione By the method of Example 22, the title product of Preparation 40 is converted to present title product.

EXAMPLE 49

5-[4-[3-(5-Methyl-2-phenyl-4-oxazolyl)propylthio]benzyl]thiazolidine-2,4-dione

By the method of Example 9, the title product of the preceding Example is converted to present title product.

EXAMPLES 50-55

5-[x-[2-(5-Methyl-2-phenyl-4-oxazolyl)ethylthio]-y-heteroarylmethylene]thiazolidine-2,4-diones By the method of Example 22, the appropriate x-[2-(5-methyl-2-phenyl-4-oxazolyl)ethylthio]heteroaryl-y-carbaldehydes are converted to the following title products:

| Example No. | x | y-Heteroaryl |
|---|---|---|
| 50 | 5 | 2-furyl |
| 51 | 5 | 2-thienyl |
| 52 | 2 | 5-pyridyl |
| 53 | 5 | 2-pyridyl |
| 54 | 5 | 1-methyl-2-pyrrolyl |
| 55 | 5 | 1-benzyl-2-pyrrolyl |

EXAMPLES 56-61

5-[x-[2-(5-Methyl-2-phenyl-4-oxazolyl)ethylsulfonyl]-y-heteroarylmethylene]thiazolidine-2,4-diones By the method of Example 10, the products of Examples 50-55 are converted to present title products as follows:

| Example No. | x | y-Heteroaryl |
|---|---|---|
| 56 | 5 | 2-furyl |
| 57 | 5 | 2-thienyl |
| 58 | 2 | 5-pyridyl |
| 59 | 5 | 2-pyridyl |
| 60 | 5 | 1-methyl-2-pyrrolyl |
| 61 | 5 | 1-benzyl-2-pyrrolyl |

EXAMPLES 62-67

5-[x-[2-(5-Methyl-2-phenyl-4-oxazolyl)ethylsulfonyl]-y-heteroarylmethyl]thiazolidine-2,4-diones By the method of Example 5, the title products of Examples 56-61 are converted to present title products as follows:

| Example No. | x | y-Heteroaryl |
|---|---|---|
| 62 | 5 | 2-furyl |
| 63 | 5 | 2-thienyl |
| 64 | 2 | 5-pyridyl |
| 65 | 5 | 2-pyridyl |
| 66 | 5 | 1-methyl-2-pyrrolyl |
| 67 | 5 | 2-pyrrolyl |

Note that in Example 67, hydrogen uptake is sufficient for hydrogenolysis of the 1-benzyl group, as well as the double bond.

EXAMPLE 68

5-[4-[N-Methyl-2-(5-methyl-2-phenyl-4-oxazolyl)acetamido]benzyl]thiazolidine-2,4-dione 2-(5-Methyl-2-phenyl-4-oxazolyl) acetic acid (0.195 g, 0.90 mmol) and SOCl$_2$ (0.109 g, 0.90 mmol) were combined in 0.67 mL of benzene and heated near reflux for 20 minutes to form a clear solution of the corresponding acid chloride. The mixture was cooled, stripped of solvent, and twice restripped from 10 mL portions of CCl$_4$. The resulting solid residue was slurred in 3 mL benzene and added portionwise to a solution of 5-[4-(methylamino) benzyl]thiazolidine-2,4-dione (0.21 g, 0.88 mmol) in 1.5 mL of pyridine maintained at 0°–5° C. The mixture was stirred 18 hours at room temperature, diluted with 40 mL of water, acidified with 6N HCl and extracted 2×40 mL ethyl acetate. The organic layers were combined, washed in sequence 1×20 mL 1N, 2×30 mL H$_2$O and 1×30 mL saturated NaCl, dried (Na$_2$SO$_4$), stripped to 0.355 g of a gum. The latter wash flash chromatographed on silica gel using ethyl acetate as eluant to yield 0.160 g of present title product as a solid; tlc Rf 0.35 (ethyl acetate).

PREPARATION 1

Ethyl 2-(Hydroxyimino)-3-oxobutyrate

Under N$_2$, a solution of ethyl acetoacetate (286 mL, 292 g, 2.24 mol) dissolved in 300 mL of acetic acid was cooled to −10° C. Maintaining that temperature, NaNO$_2$ (80 g, 2.61 mol) in 400 mL of water was slowly added, and the mixture then stirred 30 minutes at 0° C., at which time KCl (160 g, 2.15 mol) in 800 mL of water was added over 20 minutes, the mixture stirred for an additional 30 minutes at 0° C. and then extracted 3×1 L ether. The organic layers were combined, washed 2×1 L water and 1×1L brine, dried (MgSO$_4$) and stripped to yield 343.3 g (96%) of title product as an oil; tlc Rf 0.3 (1:19 CH$_3$OH:CHCl$_3$).

PREPARATION 2

Ethyl 5-Methyl-2-phenyloxazole-4-carboxylate-1-oxide Hydrochloride

Title product of the preceding Preparation (343 g, 2.16 mol) was dissolved in 550 mL of acetic acid. Benzaldehyde (285 mL, 297.5 g, 2.81 mol) was then added, the mixture cooled to 0° C., and dry HCl bubbled into the stirred reaction mixture at a moderate rate for 2 hours at 0° C. The mixture was diluted with 3 volumes of ether and filtered to yield 620 g (558 g, 90% on a dry basis) of ether wet title product, which was immediately bottled and stored at refrigerator temperature; tlc Rf 0.45 (1:19 CH$_3$OH:CHCl$_3$).

PREPARATION 3

Ethyl 5-Methyl-2-phenyloxazole-4-carboxylate

Title product of the preceding Preparation (205 g, dry basis, 0.723 mol) was dissolved in 1L of ethanol and 120 mL of methanol and hydrogenated in a Paar shaker over 14 g of 10% Pd/C at 50 psig and room temperature for 3 hours, by which time uptake of hydrogen was complete. Catalyst was recovered by filtration over diatomaceous earth with methanol wash. The filtrate and wash liquors were combined and stripped to yield present title product as an oil; tlc Rf 0.7 (1:19 $CH_3OH:CHCl_3$).

PREPARATION 4

5-Methyl-2-phenyloxazole-4-methanol

Under $N_2$, $LiAlH_4$ (11.1 g, 0.293 mol) was slurried in 300 mL ether and cooled to 0° C. A clarified solution of the title product of the preceding Preparation (67.0 g, 0.29 mol) in 300 mL of ether was added to the hydride slurry over 30 minutes, maintaining the temperature at 0-10° C. The reaction mixture was stirred 1 hour at room temperature, then diluted with 200 mL THF, slowly quenched with 11.1 mL water (vigorous gas evolution), then with 1N NaOH (11.1 mL) and finally with 33 mL additional water. The mixture was stirred 15 minutes, diluted with 200 mL additional THF, filtered and the filtrate stripped to yield 46 g (84%) of present title product as a solid; tlc Rf 0.4 (1:19 $CH_3OH:CHCl_3$).

PREPARATION 5

5-Methyl-2-phenyloxazole-4-carbaldehyde

Pyridinium dichromate $(C_6H_5N)_2 \cdot H_2Cr_2O_7$, 120.8 g, 0.324 mol) was added to a solution of the title product of the preceding Preparation (20.4 g, 0.106 mol) in 500 mL of $CH_2Cl_2$ and the slurry stirred for 7 hours, diluted with 1L of ether, filtered over diatomaceous earth, and the filtrate stripped to yield 14.1 g (70%) of present title product; tlc Rf 0.75 (3:1 ethyl acetate:hexane).

PREPARATION 6

(5-Methyl-2-phenyl-4-oxazolyl)methyl Azide

Under $N_2$, to a stirred solution of the title product of Preparation 4 (10.0 g, 0.053 mol) was added in sequence triphenylphosphine (18.0 g, 0.069 mol), $NaN_3$ (10.3 g, 0.159 mol) and $CCl_4$ (15.3 mL, 0.159 mol). The mixture, which was initially mildly exothermic, was stirred for 1 hour, then poured into 400 mL of water and extracted 2×300 mL ether. The organic layers were combined, extracted 2×300 mL water and 1×300 mL brine, dried ($MgSO_4$), stripped, and the sticky solid residue flash chromatographed on silica gel using 4:1 hexane:ethyl acetate as eluant to yield 7.77 g (68%) of present title product as an oil which crystallized on standing; tlc Rf 0.8 (1:19 $CH_3OH:CHCl_3$).

PREPARATION 7

N-[(Methyl-2-phenyl-4-oxazolyl)methyl]amine

Under $N_2$, a stirred slurry of $LiAlH_4$ ( 0.96 g, 0.025 mol) in 75 mL of ether was cooled to −5° C., title product of the preceding Preparation (3.05 g, 0.014 mol) in 40 mL of ether was added over 15 minutes. The mixture was allowed to warm, then heated at reflux for 3 hours, cooled to 0° C., and diluted with 3 mL saturated $Na_2SO_4$. The resulting slurry was filtered with ether and THF wash. The filtrate and wash liquors were combined, dried ($MgSO_4$) and stripped to yield 2.2 g (82%) of present title product as an oil; tlc Rf 0.0 (1:19 $CH_3OH:CHCl_3$).

PREPARATION 8

N-Methyl-N-[(5-methyl-2,phenyl-4-oxazolyl)methyl]amine

Title product of Preparation 5 (2.0 g, 10.7 mmol) was combined with $MgSO_4$ (2 g) in 50 mL ether, cooled to 0° C. and the mixture saturated with gaseous methylamine. The mixture was stirred 15 minutes at 0° C., then at room temperature for 3 hours, filtered over diatomaceous earth with ether wash, and the combined filtrate and wash liquors stripped to yield intermediate imine as an oil. All of this oil was taken up in 50 mL $CH_3OH$ and cooled to 0° C. $NaBH_4$ (2.2 g, 0.058 mmol) was added and the mixture stirred at 0° C. for 15 minutes, then at room temperature for 18 hours. The mixture was diluted with 2 volumes of water and extracted 2×150 mL ethyl acetate. The organic layers were combined, washed 2×150 mL water and 1×150 mL brine, and stripped to yield 1.54 g (46%) of present title product as an oil; tlc Rf 0.0 (1:19 $CH_3OH:CHCl_3$).

PREPARATION 9

5-(Phenylmethylene)thiazolidine-2,4-dione

Benzaldehyde (0.78 mol, 82.8 g) and 2,4-thiazolidinedione (0.85 mol, 100 g) were heated to reflux in a mixture of pyridine (215 mL) and dimethylformamide (400 ml) for 18 hours. The reaction mixture was cooled to 55° C., diluted with hexane (360 mL) and water (900 mL), and stirred for 1 hour after cooling to room temperature. The product was collected to afford 175 g of title product as a pale yellow solid; mp 246°–248° C.

PREPARATION 10

5-(Benzyl)thiazolidine-2,4-dione

The title product of the preceding Preparation (0.12 mol, 25 g) was hydrogenated in a Paar shaker at 50 psig for 18 hours at room temperature using 10% Pd/C (25 g of 50 wt% $H_2O$) in tetrahydrofuran (750 mL) and acetic acid (250 mL). The catalyst was removed by filtration and the solvent removed in vacuo. The crude solid was recrystallized from ethanol:water (1:2) to afford 15.4 of pale grey crystals; mp 101°–103° C.

Analysis calculated for $C_{10}H_9O_2NS$: C, 57.95; H, 4.38; N, 6.76%. Found: C, 57.95; H, 4.30; N, 6.76%.

PREPARATION 11

4-[(Thiazolidine-2,4-dion-5-yl)methyl]-benzenesulfonyl Chloride

Chlorosulfonic acid (5 mL) was cooled to 0° C. and the 5-benzyl-2,4-thiazolidinedione prepared above (9.6 mmol, 2.0 g) was added portionwise. The reaction mixture was stirred at room temperature for 0.5 hour and poured into ice (25 g). The solution was extracted with methylene chloride (2×50 mL), the organic layers were combined and dried ($Na_2SO_4$), and solvent removed in vacuo to afford title product which was used without further purification.

PREPARATION 12

4-[(5-Methyl-2-phenyl-4-oxazolyl)methylaminocarbonyl]benzaldehyde

Under $N_2$, 4-carboxybenzaldehyde (0.934 g, 6.22 mmol), 30 mL THF and triethylamine (0.87 mL, 6.24 mmol) were combined and the resulting solution cooled to 0° C. Isobutylchloroformate (0.81 mL, 6.24 mmol) was added, forming a white milky slurry which was stirred 30 minutes at 0° C. to fully form the mixed anhydride. Title product of Preparation 7 (1.17 g, 6.22 mmol) in 15 mL THF was added dropwise to over 5 minutes and stirring continued for 30 minutes at 0° C. and then at room temperature for 18 hours. The reaction mixture was quenched with an equal volume of water and then with an equal volume of 1N NaOH, and extracted 2×125 mL ethyl acetate. The organic layers were combined, washed 2×125 mL water and 2×125 mL brine, dried ($MgSO_4$), stripped to an oil (2.01 g) and flash chromatographed on silica gel using 3:1 ethyl acetate:hexane as eluant to yield 1.10 g of purified title product in the form of yellow crystals; tlc Rf 0.55 (3:1 ethyl acetate:hexane).

PREPARATION 13

4-[N-[(5-Methyl-2-phenyl-4-oxazolyl)methyl]methylaminocarbonyl]benzaldehyde

By the method of the preceding Preparation, the title product of Preparation 8 (1.5 g, 7.42 mmol) was converted to 0.52 g present chromatographed title product, tlc Rf 0.4 (3:1 ethyl acetate:hexane).

PREPARATION 14

Methyl 2-(Benzoylamino)-3-oxobutyrate

L-Aspartic acid beta-methyl ester hydrochloride (5.0 g, 0.027 mol) was partially dissolved in 15 mL of pyridine by stirring for 15 minutes at room temperature, and the mixture cooled to 0° C. With vigorous stirring, benzoyl chloride (3.1 mL, 3.8 g, 0.027 mol) was then added dropwise, and stirring continued for 1.5 hours at 0° C. and 0.5 hour at room temperature to yield a solution of intermediate N-benzoyl L-aspartic acid beta-methyl ester. Acetic anhydride (10 mL) was added and the mixture heated at 90° C. for 2 hours, then diluted with 15 mL of water and heating continued for 15 minutes. The mixture was cooled, acidified with excess dilute HCl and extracted 2×75 mL of ethyl acetate. The organic layers were combined, washed in sequence with 1×50 mL 2N HCl, 1×50 mL water, 3×50 mL saturated $NaHCO_3$, 1×50 mL water and 1×50 mL saturated NaCl, dried over $Na_2SO_4$ and stripped to yield 4.3 g of present title product as a thick oil; tlc Rf 0.75 (9:1 $CH_2Cl_2$:$CH_3OH$), 0.25 (49:1 $CH_2Cl_2$:$CH_3OH$), 0.15 (1:2 ethyl acetate:hexane).

PREPARATION 15

Methyl 2-(5-Methyl-2-phenyl-4-oxazolyl)acetate

Phosphorus oxychloride (20 mL) was added to a solution of title product of the preceding Preparation in 80 mL of toluene and the mixture heated at reflux for 4 hours, cooled to room temperature, poured into 200 mL of ice and water, adjusted to pH 7.5 with solid $K_2CO_3$ and extracted 2×100 mL ether. The organic layers were combined, washed 1×100 mL water and 1×100 mL saturated NaCl, stripped to 2.4 g of an oil, and the latter flash chromatographed on silica gel with 1:2 ethyl acetate:hexane as eluant to yield 1.1 g of purified, present title product as an oil; tlc Rf 0.4 (1:2 ethyl acetate:hexane).

PREPARATION 16

2-(5-Methyl-2-phenyl-4-oxazolyl) acetic Acid

Title product of the preceding Preparation (1.1 g, 4.8 mmol) was slurried in 15 mL of 1N NaOH and heated at gentle reflux for 0.5 hour. The resulting solution was cooled to 0°-5° C. and acidified with excess 6N HCl to precipitate 0.82 g of present title product; tlc Rf 0.05 (1:1 ethyl acetate:hexane), 0.2 (1:2 ethyl acetate:hexane).

PREPARATION 17

2-(5-Methyl-2-phenyl-4-oxazolyl)ethyl Bromide 2-(5-Methyl-2-phenyl-4-oxazolyl)ethanol (0.203 g, 1.0 mmol; European patent application 177353) and $CBr_4$ (0.662 g, 2.0 mmol) were dissolved in 10 mL of ether and cooled to 0° C. Triphenylphosphine (0.524 g, 2.0 mmol) was added and the mixture stirred for 3 hours at room temperature. The mixture was filtered, the filtrate was stripped of solvent and the residue filtered through a plug of silica gel using $CHCl_3$ as eluant to yield 0.16 g of present title product as a white solid; mp 59°-61° C.; tlc Rf 0.22 ($CHCl_3$).

PREPARATION 18

4-[2-(5-Methyl-2-phenyl-4-oxazolyl)ethylthio]phenyl Bromide

NaH (46 mg, 1.92 mmol) was added to 8 mL THF at 0° C. and stirred for 5 minutes. 4-Bromothiophenol (278 mg, 1.47 mmol) was added and the mixture stirred for 15 minutes at 0° C. to form the sodium salt. Finally title product of the preceding Preparation (300 mg, 1.13 mmol) was added and the mixture stirred 1 hour at 0° C. and 2 hours at room temperature, then diluted with 20 mL ethyl acetate, washed 1×15 mL water and 1×15 mL saturated NaCl, dried ($MgSO_4$), stripped and the residue plug filtered on silica gel using 2:1 hexane:ether as eluant to yield 0.26 g of present title product as a white solid; mp 51°-53° C.

PREPARATION 19

4-[2-(5-Methyl-2-phenyl-4-oxazolyl)ethylthio]benzaldehyde

The title product of the preceding Preparation (0.50 g, 1.34 mmol) was dissolved in 15 mL of dry, distilled THF and cooled to −78° C. n-Butyllithium (0.7 mL of 2.1M in hexane, 1.47 mmol) was added and the mixture stirred 15 minutes at −78° C. DMF (0.30 mL, 3.9 mmol) was then added and the mixture allowed to warm to room temperature, poured into 50 mL of water and extracted 3×60 mL ether. The organic layers were combined, dried ($MgSO_4$) and stripped to 0.45 g of oil. The latter was plug filtered on silica gel using 2:1 hexane:ether as eluant to yield 0.25 g of present title product as a white solid; mp 74°-76° C.; tlc Rf 0.2 (2:1 hexane:ether).

PREPARATIONS 20-26

2-[5-Methyl-2-(substituted) -4-oxazolyl]acetic Acids

Substituting the appropriate acid chlorides for benzoyl chloride in the sequence of Preparations 14-16, the following additional 2-(5-methyl-2-(substituted)-4-oxazolyl]acetic acids are prepared.

| Preparation No. | 2-Substituent |
|---|---|
| 20 | 4-methoxyphenyl |
| 21 | 2,5-dichlorophenyl |
| 22 | 3-fluoro-4-methylphenyl |
| 23 | 2-thienyl |
| 24 | 2-furyl |
| 25 | 3-furyl |
| 26 | 5-bromo-2-furyl |

PREPARATIONS 27–39

4-[(Heteroaryl)methylthio]benzaldehydes

By substituting the appropriate (heteroaryl)methyl halide for 2-(5-methyl-2-methyl-4-oxazolyl)ethyl bromide, the sequential methods of Preparations 18 and 19 are used to prepare the following title compounds:

| Preparation No. | Heteroaryl Group |
|---|---|
| 27 | 5-methyl-2-phenyl-4-oxazolyl |
| 28 | 2-phenyl-4-oxazolyl |
| 29 | 2-(4-methoxyphenyl)-5-methyl-4-oxazolyl |
| 30 | 2-(2-thienyl)-5-methyl-4-oxazolyl |
| 31 | 2-(2-furyl)-5-methyl-4-oxazolyl |
| 32 | 2-cyclohexyl-5-methyl-4-oxazolyl |
| 33 | 2-phenyl-4-thiazolyl |
| 34 | 4-methyl-2-phenyl-5-thiazolyl |
| 35 | 2-pyridyl |
| 36 | 4-pyridyl |
| 37 | 5-phenyl-2-furyl |
| 38 | 5-phenyl-2-thienyl |
| 39 | 1-methyl-5-phenyl-2-pyrrolyl |

PREPARATION 40

4-[3-(5-Methyl-2-phenyl-4-oxazolyl)propylthio]benzaldehyde

The sequential methods of Preparations 18 and 19 are used to convert 3-(5-methyl-2-phenyl-4-oxazolyl)propyl bromide to present title product.

PREPARATIONS 41–46 x-[2-(5-Methyl-2-phenyl-4-oxazolyl)ethylthio]-heteroaryl-y-carbaldehydes

By the sequential methods of Preparations 18 and 19, the appropriate x-mercapto-y-bromo- heteroaryl compounds are converted to the following title compounds:

| Preparation No. | x | Heteroaryl | y |
|---|---|---|---|
| 41 | 5 | furan | 2 |
| 42 | 5 | thiophene | 2 |
| 43 | 2 | pyridine | 5 |
| 44 | 5 | pyridine | 2 |
| 45 | 5 | 1-methylpyrrole | 2 |
| 46 | 5 | 1-benzylpyrrole | 2 |

PREPARATION 47

5-[4-(Methylamino)benzyl]thiazolidine-2,4-dione

To acetic anhydride (1.2 g, 11.7 mmol) cooled to 0°–5° C. was added dropwise formic acid (0.663 g, 14.4 mmol) and the mixture then heated at 50°–55° C. for 2 hours, cooled to room temperature and diluted with 5 mL of THF. 5-(4-Aminobenzyl)thiazolidine-2,4-dione (1.0 g, 4.5 mmol) was added and the mixture stirred overnight to form intermediate 5-[4-(formylamino)benzyl]oxazolidine-2,4-dione. The volatiles were stripped in vacuo, the residue taken up in 5 mL THF, cooled to 0°–5° C., and $BH_3 \cdot (CH_3)_2S$ (5.75 mL of 2.0M in THF, 11.5 mmol) added with continued cooling (Note: gas evolution). The reaction mixture was then heated to reflux for 3 hours, cooled to room temperature, diluted with 10 mL $CH_3OH$, stirred 1 hour, cooled to 0°–5° C., adjusted to pH 2 by bubbling dry HCl into the solution, reheated at reflux for 1 hour, cooled and finally stripped of solvent. The residue was taken up in 75 mL saturated $NaHCO_3$ and extracted 2×50 mL ethyl acetate. The organic layers were combined, washed 1 x 40 mL H20 and 1×40 mL saturated NaCl, dried ($Na_2SO_4$) and stripped to yield 1.4 g of present title product as an oil; tlc Rf 0.7 (ethyl acetate).

We claim:

1. A compound of the formula

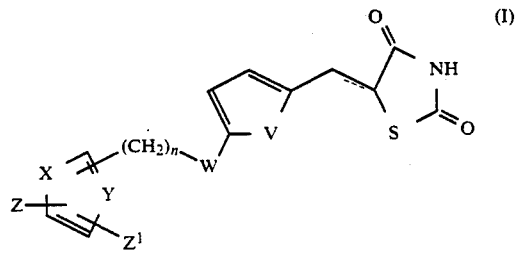

wherein
the dotted line represents a bond or no bond;
V is —CH=CH—, —N=CH—, —CH=N—, S, O or NR;
W is S, SO, $SO_2$, $SO_2NR^1$, $NR^1SO_2$, $CONR^1$ or $NR^1CO$;
X is S, O, $NR^2$, —CH=N— or —N=CH;
Y is CH or N;
Z is hydrogen, ($C_1$-$C_7$)alkyl, ($C_3$-$C_7$)cycloalkyl, phenyl, pyridyl, furyl, thienyl or phenyl mono- or disubstituted with the same or different groups which are ($C_1$-$C_3$)alkyl, trifluoromethyl, ($C_1$-$C_3$)alkoxy,fluoro, chloro or bromo;
$Z^1$ is hydrogen or ($C_1$-$C_3$)alkyl;
R, $R^1$ and $R^2$ are each independently hydrogen or ($C_1$-$C_4$) alkyl; and
n is 1, 2 or 3;
a pharmaceutically acceptable cationic salt thereof; or a pharmaceutically acceptable acid addition salt thereof when the compound contains a basic nitrogen.

2. A compound of the formula

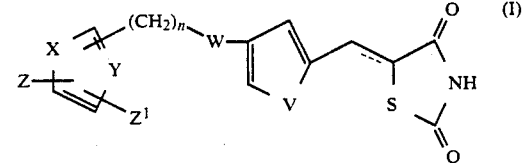

wherein
the dotted line represents no bond;
V is —CH=CH—,
W is $CONR^1$ or $NR^1CO$;
X is S, O, $NR^2$, —CH=N— or —N=CH;
Y is CH or N;
Z is hydrogen, ($C_1$-$C_7$)alkyl, ($C_3$-$C_7$)cycloalkyl, phenyl, pyridyl, furyl, thienyl or phenyl mono- or disubstituted with the same or different groups which are $(C_1-C_3)$alkyl, trifluoromethyl, $(C_1-C_3)$alkoxy, fluoro, chloro or bromo;

$Z^1$ is hydrogen or $(C_1-C_3)$alkyl;

$R^1$ and $R^2$ are each independently hydrogen or $(C_1-C_4)$alkyl; and n is 1 or 2; and a pharmaceutically acceptable cationic salt thereof; or a pharmaceutically acceptable acid addition salt thereof when the compound contains a basic nitrogen.

3. A compound of claim 1 wherein the dotted line represents no bond.

4. A compound of claim 3 wherein V is —CH=CH— and n is 1 or 2.

5. A compound of claim 2 wherein n is 1 and W is $CONR^1$.

6. A compound of claim 5 wherein X is O and Y is N forming an oxazol-4-yl group.

7. The compound of claim 6 wherein $R^1$ is hydrogen, Z is 2-phenyl and $Z^1$ is 5-methyl.

8. A compound of claim 2 wherein n is 1, and W is $NR^1CO$.

9. A compound of claim 8 wherein X is O and Y is N forming an oxazol-4-yl group.

10. The compound of claim 9 wherein $R^1$ is hydrogen, Z is 2-phenyl and $Z^1$ is 5-methyl.

11. The compound of claim 9 wherein $R^1$ is methyl, Z is 2-phenyl and $Z^1$ is 5-methyl.

12. A compound of claim 4 wherein n is 2 and W is S or $SO_2$.

13. A compound of claim 12 wherein W is S, X is O and Y is N forming an oxazol-4-yl group.

14. The compound of claim 13 wherein Z is 2-phenyl and $Z^1$ is 5-methyl.

15. A compound of claim 12 wherein W is $SO_2$, X is and Y is N forming an oxazol-4-yl group.

16. The compound of claim 15 wherein Z is 2-phenyl and $Z^1$ is 5-methyl.

17. A pharmaceutical composition for use in a hyperglycemic mammal which comprises a blood glucose lowering amount of a compound of claim 1 and a pharmaceutically acceptable carrier.

18. A pharmaceutical composition for use in a hyperglycemic mammal which comprises a blood glucose lowering amount of a compound of claim 3 and a pharmaceutically acceptable carrier.

19. A pharmaceutical composition for use in a hyperglycemic mammal which comprises a blood glucose lowering amount of a compound of claim 4 and a pharmaceutically acceptable carrier.

20. A method of lowering the blood glucose in a hyperglycemic mammal which comprises administering to said mammal a blood glucose lowering effective amount of a compound of claim 1.

21. A method of lowering the blood glucose in a hyperglycemic mammal which comprises administering to said mammal a blood glucose lowering effective amount of a compound of claim 3.

22. A method of lowering the blood glucose in a hyperglycemic mammal which comprises administering to said mammal a blood glucose lowering effective amount of a compound of claim 4.

23. A pharmaceutical composition for use in a hypercholesterolemic mammal which comprises a blood cholesterol lowering amount of a compound of claim 1 and a pharmaceutically acceptable carrier.

24. A pharmaceutical composition for use in a hypercholesterolemic mammal which comprises a blood cholesterol lowering amount of a compound of claim 3 and a pharmaceutically acceptable carrier.

25. A pharmaceutical composition for use in a hypercholesterolemic mammal which comprises a blood cholesterol lowering amount of a compound of claim 4 and a pharmaceutically acceptable carrier.

26. A method of lowering the blood cholesterol in a hypercholesterolemic mammal which comprises administering to said mammal a blood cholesterol lowering effective amount of a compound of claim 1.

27. A method of lowering the blood cholesterol in a hypercholesterolemic mammal which comprises administering to said mammal a blood cholesterol lowering effective amount of a compound of claim 3.

28. A method of lowering the blood cholesterol in a hypercholesterolemic mammal which comprises administering to said mammal a blood cholesterol lowering effective amount of a compound of claim 4.

* * * * *